United States Patent
Ando et al.

Patent Number: 5,422,483
Date of Patent: Jun. 6, 1995

[54] NEAR INFRARED ANALYZER

[75] Inventors: Osamu Ando; Atsuhiro Iida; Kan Nakamura, all of Kyoto; Yasuo Tsukuda, Osaka, all of Japan

[73] Assignee: Shimadzu Corporation, Nakagyo, Japan

[21] Appl. No.: 88,453

[22] Filed: Jul. 7, 1993

[30] Foreign Application Priority Data

Jul. 31, 1992 [JP] Japan ................................. 4-224996

[51] Int. Cl.[6] .......................................... G01N 21/35
[52] U.S. Cl. ...................... 250/339.02; 250/339.07; 250/339.11; 250/341.1; 250/341.8
[58] Field of Search ................ 250/339, 341, 338.5, 250/339.02, 339.11, 339.07, 341.1, 341.8; 356/236, 328

[56] References Cited

U.S. PATENT DOCUMENTS

| | | | |
|---|---|---|---|
| 3,874,799 | 1/1975 | Isaacs et al. | 356/236 |
| 4,674,880 | 6/1987 | Seki | 356/328 |
| 4,800,280 | 1/1989 | Satake | 250/339 |
| 4,932,779 | 6/1990 | Keane | 356/236 |
| 4,968,143 | 11/1990 | Weston | 356/236 |
| 5,017,785 | 5/1991 | Räsänen | 250/345 |
| 5,206,701 | 4/1993 | Taylor et al. | 356/325 |

*Primary Examiner*—Constantine Hannaher
*Attorney, Agent, or Firm*—Heller, Ehrman, White & McAuliffe

[57] ABSTRACT

A near infrared analyzer has, arranged on a base, a halogen tungsten lamp as light source, an optical stop for light from the source, an optical system for converging a flux of light for measuring and directing it to a measuring section and a system including an integrating sphere at which a sample is set. A spectrometer part has its entrance slit placed on the bottom surface of the integrating sphere, and includes a diffraction grating for diffraction and dispersion of incident light flux from the entrance slit, an arrayed detector and a reflective mirror for reflecting the diffracted light from the diffraction grating so as to be dispersed and focused on the surface of the detector. Signals from the detector can be sequentially retrieved for electronically scanning wavelengths without mechanically oscillating or rotating the grating. This makes it possible to maintain high accuracy in wavelengths over a long period of time. As the speed of measurement is increased, measurements can be repeated and obtained data integrated for reducing noise and improving accuracy of measurement.

20 Claims, 4 Drawing Sheets

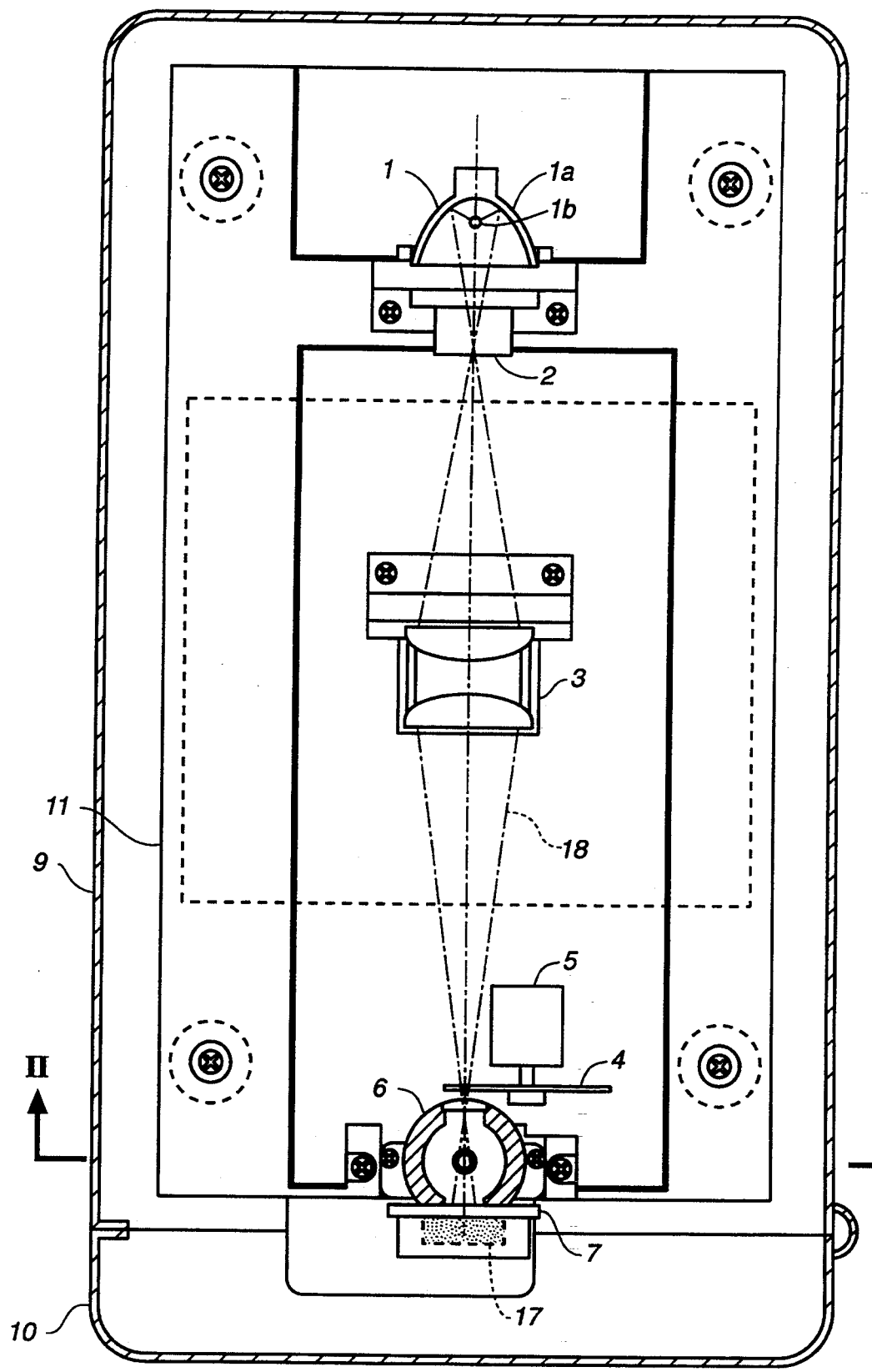
FIG._1

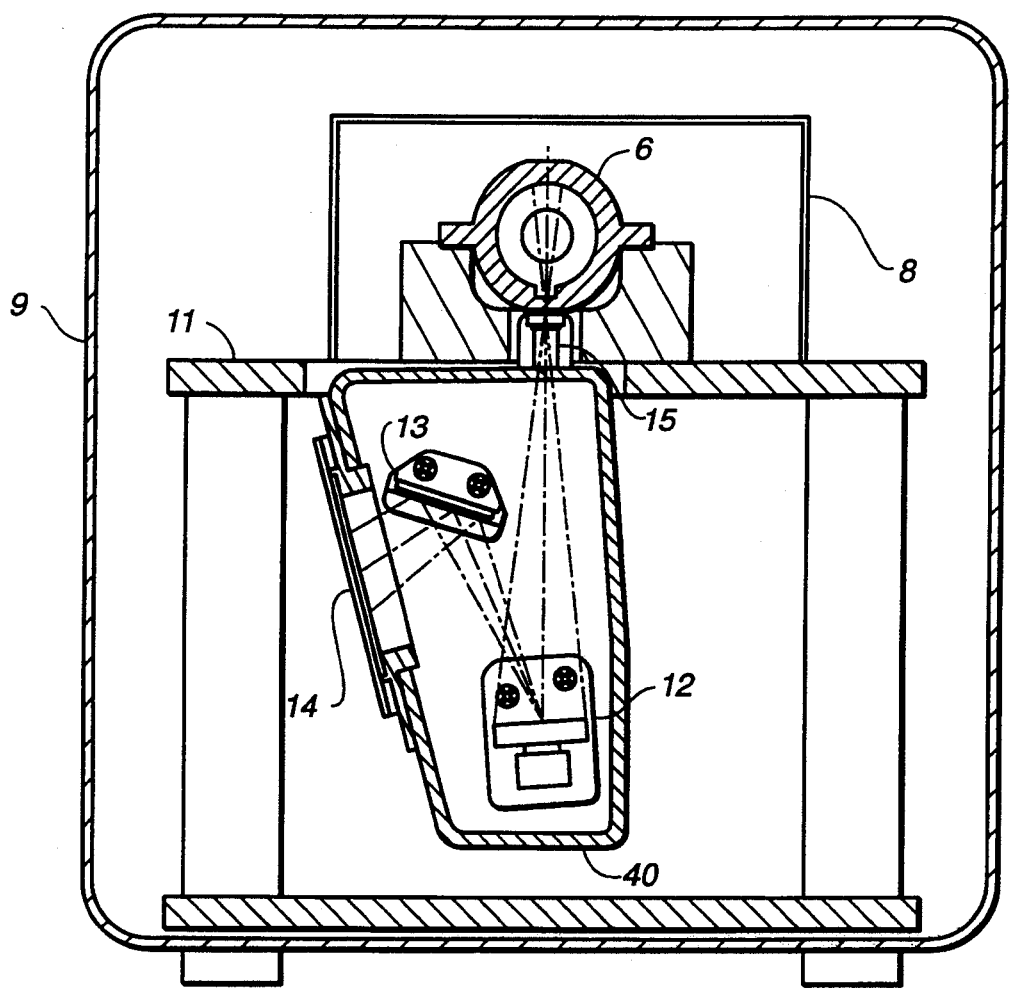
FIG._2
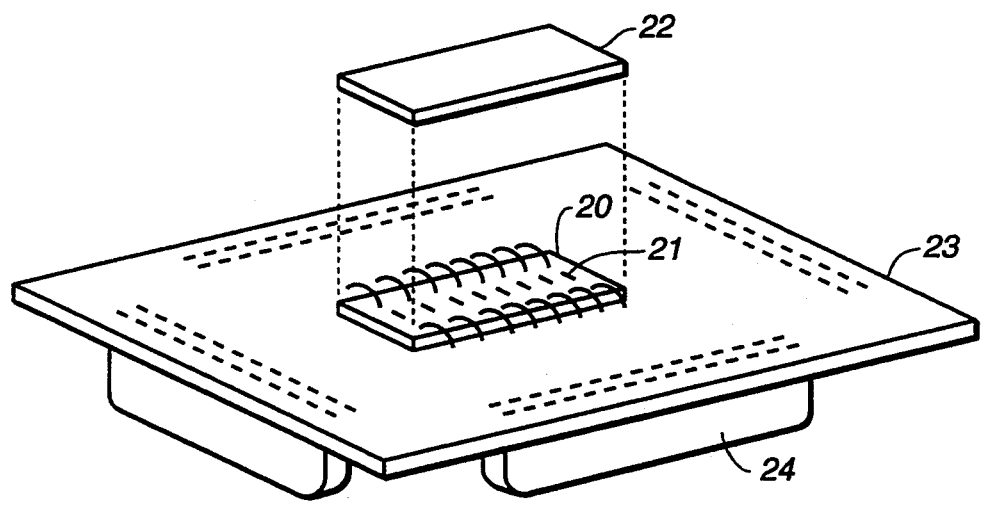
FIG._4

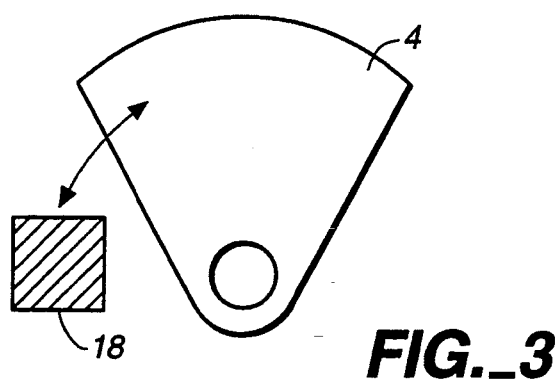
FIG._3
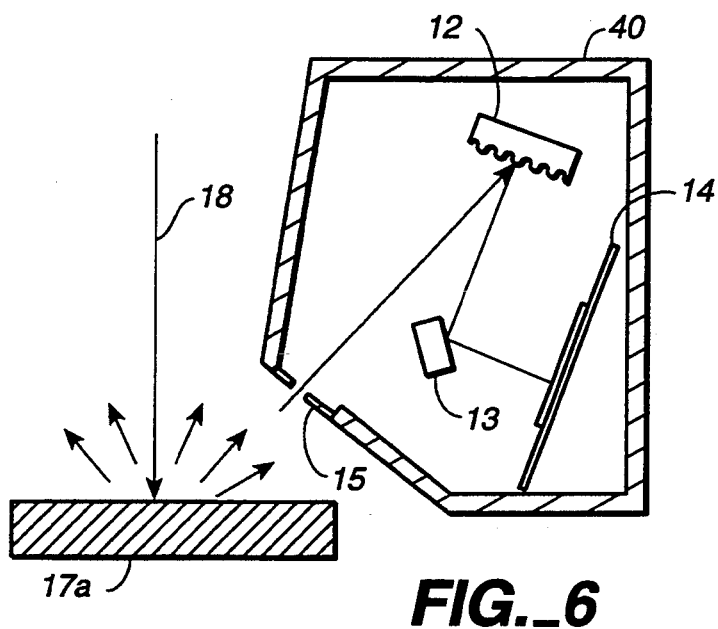
FIG._6
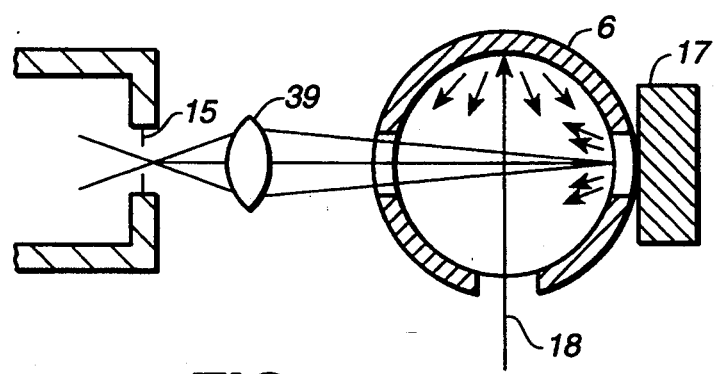
FIG._7

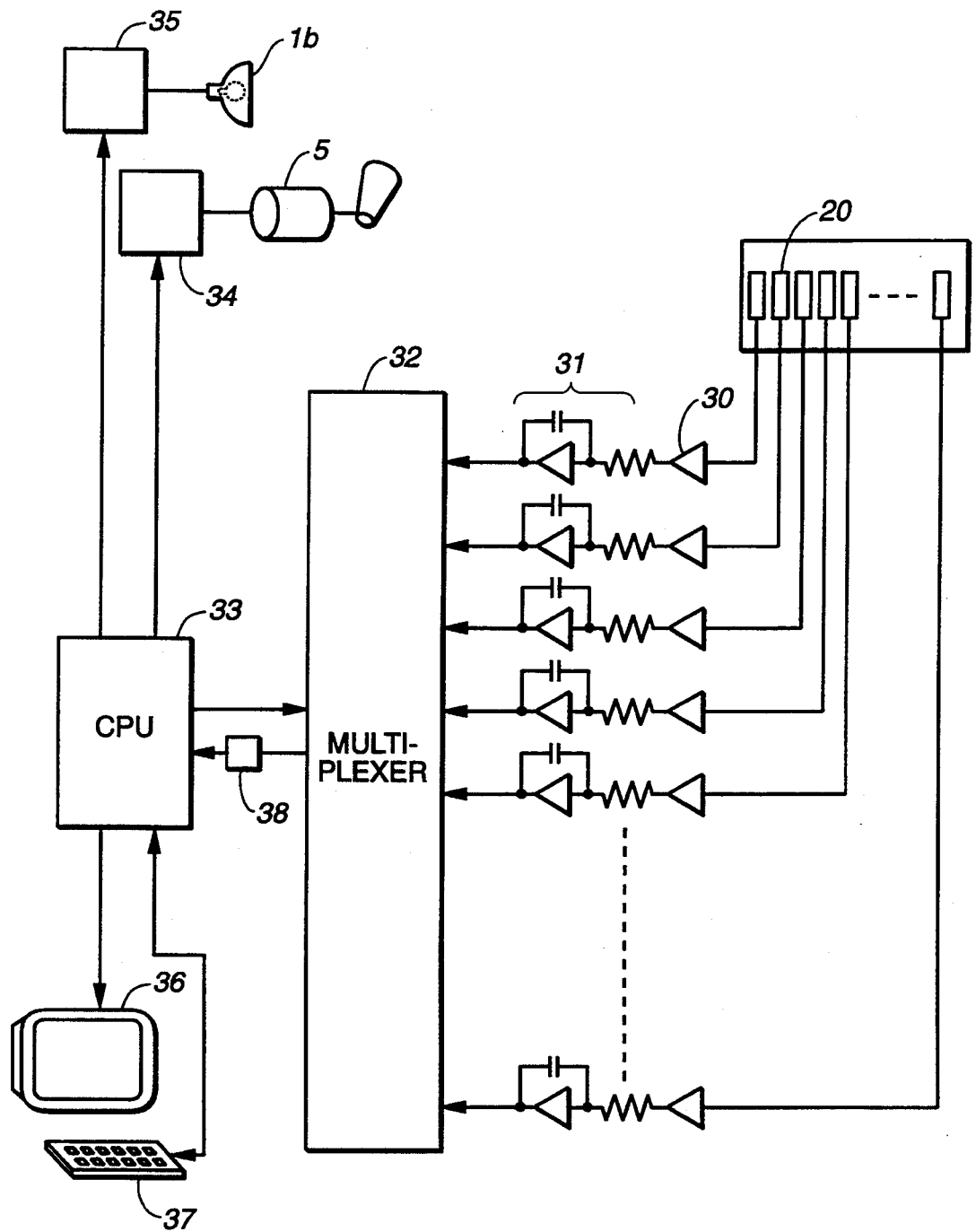
FIG._5

NEAR INFRARED ANALYZER

BACKGROUND OF THE INVENTION

This invention relates to a near infrared analyzer for quantitative and/or qualitative analysis of a sample by measuring the optical characteristics of its transmitted and/or reflected light in a near infrared region. Analyzers of this kind have been in use for measuring spectroscopic characteristics, for example, of agricultural products, processed foods, chemical substances and medicines against light.

Near infrared analyzers were developed initially as an apparatus for analyzing the protein and water content of wheat and have since come to be used extensively for the analysis of processed foods, liquors, products of chemical industries and medicines. When a near infrared analyzer is used for analysis, the sample is generally not pretreated chemically, that is, the sample is usually used in the apparatus in a non-destructed condition. According to an exemplary method of quantitative analysis, an absorption or reflection spectrum of an unknown sample is measured over a certain range of wavelength principally in the near infrared region or at a plurality of near infrared wavelengths, and the content of a desired component is obtained by using the spectral data with a preliminarily prepared predictive formula. For a simultaneous quantitative analysis of a plurality of components, predictive formulas are individually prepared for the desired components and individually applied to the spectral data. Such predictive formulas are prepared by a statistical method from the spectral data of a plurality of samples with a variety of known contents. Where a quantitative analysis is the objective, such formulas may be prepared, say, by a multiple regression analysis. These predictive formulas are similar to what is commonly known as the detection line in ordinary instrumental analyses but involve much more complicated calculations.

Since such analyzers are used principally for sorting agricultural products and quality control of processed foods, they mostly perform analyses of similar kinds many times day in and day out. Since the results of these measurements are very important in the quality control and determination of the prices of the measured samples, the analyzers must be able to perform the measurements speedily, their accuracy must be at least as good as by prior art methods of chemical analyses, and stability must be high both on a long-term basis and on a short-term basis.

From the point of view of the structure of spectroscopic elements to be used, prior art analyzers which have been used to satisfy these requirements can be classified into the kind which scans a wavelength band of the detection light and the kind which performs measurements at a fixed wavelength. The latter is characterized by the a plurality of band pass filters within a narrow band which are sequentially inserted into an optical path such that absorptivity can be measured at a plurality of wavelengths. Analyzers of the latter (fixed wavelength) kind are advantageous in that the structure is simple and they can be inexpensive. They are disadvantageous, however, in that the wavelength cannot be freely selected for measurements and hence that the kind of samples which can be measured becomes limited, depending on the analyzer to be used.

Analyzers of the former (wavelength-scanning) kind may be characterized as having a diffraction grating and scanning a wavelength band of light emitted through an exit slit by rotating or oscillating the grating. The wavelength of the light to be used for analysis can be freely selected with an analyzer of this kind, and such an analyzer can be used for a larger variety of samples and for broader research purposes. In order to satisfy the requirements mentioned above with an analyzer of this kind with a diffraction grating, that is, to achieve high-speed measurements with high accuracy with high short-term and long-term stability, however, many improvements must be effected. For example, the optical system inclusive of a spectrometer must be designed for low optical losses, both the speed and accuracy of the scanning of the diffraction grating must be improved, and the temperature variations and vibrations of each component of the device must be reduced or compensated for. In view of the above, U.S. Pat. No. 4,283,596 disclosed an optical system using a unique cam drive structure to oscillate a diffraction grating. U.S. Pat. No. 4,540,282 disclosed a combination of a return force spring, a detector of back electromagnetic flux and a DC motor for providing a harmonic oscillation to a diffraction grating. European Patent Application Publication No. 378,108 disclosed a combination of a DC motor and an optical encoder to control the speed of the motor to oscillate a diffraction grating. In addition, it has been known, as has been used in visible-light, ultraviolet and infrared spectrophotometers, to convert the rotary motion of a motor into a linear motion by means of a feed screw and to convert it again for the rotation of a diffraction grating by means of a sine bar.

There have been problems with prior art near infrared analyzers, and in particular with those which use a diffraction grating spectrometer to scan a wavelength band by rotating or oscillating the diffraction grating. If the grating is mechanically scanned, as with all of the devices described above, a complicated power-transmitting mechanism such as a cam is necessary and, since the speed of its rotation must be increased in order to reduce the time of measurement, long-term maintenance of mechanical reliability and accuracy becomes a serious problem. In the case of devices with a combination of a DC motor and an encoder, it must be remembered that components like the encoder requiring high accuracy are extremely vulnerable to vibrations and shocks. In the case of measurements of agricultural products outdoors where there are noises and severe temperature changes, for example, there arise short-term problems of reliability. Moreover, both the motor and the encoder are rotary machine components, but bearings have a limited mechanical lifetime. One cannot forget the additional problems of deterioration in accuracy of measurements due to wears and tears of parts over a long time of use.

It is therefore an object of the present invention to provide a near infrared analyzer capable of high-speed measurements with high accuracy which is stable both on long-term and short-term bases.

SUMMARY OF THE INVENTION

A near infrared analyzer according to the present invention, with which the above and other objects can be achieved, may be characterized as comprising a light source for generating light having a continuous near infrared spectrum, a light-converging optical system for converging the light from the source and introducing it into a measuring means where the light introduced by the light-converging optical system is made incident on a sample, a spectrometer means with a diffraction grating serving to diffract approximately in a plane the light which has passed the measuring means and to focus it on an imaging plane, and an arrayed detector which is disposed on the imaging plane and sensitive in a near infrared region, and a signal processing circuit for processing signals outputted from the detector.

The aforementioned spectrometer means is provided with a diffraction grating and is so structured that wavelengths for measurement can be freely selected. Since it has no mechanical driving means, it has superior short-term and long-term reliability. Since measured data for different wavelengths can be obtained by electrically scanning the arrayed detector, the scanning operation can be accelerated, and accuracy of measurement can be improved by the integrating effect due to repeated scanning.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a plan view of a near infrared analyzer embodying the present invention;

FIG. 2 is a sectional view of the near infrared analyzer of FIG. 1 taken along the line II—II therein;

FIG. 3 is a front view of the dark vane of the near infrared analyzer of FIGS. 1 and 2;

FIG. 4 is a diagonal view of the arrayed detector of the near infrared analyzer of FIGS. 1 and 2;

FIG. 5 is a circuit diagram of the signal processing system of the near infrared analyzer of FIGS. 1 and 2;

FIG. 6 is a side sectional view of another measuring means according to the present invention; and FIG. 7 is a side sectional view of still another measuring means according to the present invention.

, DETAILED DESCRIPTION OF THE INVENTION

With reference to FIGS. 1 and 2, which are respectively a plan view and a sectional view of a near infrared analyzer embodying the present invention, numeral 1 indicates a light source having an ellipsoidal reflective mirror 1a and a source lamp 1b disposed at the first focus of the mirror 1a. The source lamp 1b is for generating light at least in a near infrared region, or more in detail, having a continuous spectrum approximately in the range of wavelength 1000–2600 nm. In view of later expansion in the utility of the analyzer, a lamp capable of also generating light in a visible wavelength range is desirable. As an example of such light source, use may be made of a tungsten-halogen lamp. The source 1 is so structured that the light-emitting point of the lamp 1b (that is, its filament) is located exactly at the position of the first focus of the ellipsoidal mirror 1a such that an image of the filament is formed at the second focus of the mirror 1a. An optical stop 2 is disposed at the second focus of the mirror 1a such that the size of the light flux for the rest of the optical system can be controlled by placing an opening of a selected dimension at the position of the image of the filament. Alternatively, the optical stop 2 may be placed at a position slightly displaced from the second focus of the mirror 1a such that a slightly out-of-focus image of the filament may be used as a secondary light source. This is for the purpose of avoiding the kind of undesirable situation which may arise if the image of the filament is formed on the surface of the sample or the diffraction grating, causing a non-uniform distribution of light intensity.

A light-converging optical system 3 is provided for focusing and introducing into the measuring means the light flux which has passed through the optical stop 2. The optical system 3 is provided with two plano-convex lenses. Since the frequency band for the measurement is about 1000–2600 nm, the loss of light due to absorption by the lenses may be significant. For this reason, lenses made of anhydrous quartz glass are preferred. The optical system 3 is not limited by the example described above. Use may be made equally well of a mirror with a spherical or non-spherical reflective surface. In such a situation, there arises no problem of light loss due to absorption by the optical element itself.

An integrating sphere 6 with an entrance window and a sample window is included in the measuring means. A sample 17 carried on a sample holder 7 is positioned at the sample window formed opposite to the entrance window. Measuring light 18 focused by the optical system 3 is introduced through the entrance window of the integrating sphere 6 and made incident on the sample 17. The measuring light 18 is adjusted so as to form an image of the optical stop 2 approximately at the position of the entrance window of the integrating sphere 6. This is so as to prevent the image of the optical stop 2 from being formed on the surface of the sample 17 disposed at, or near the sample window of the integrating sphere and to thereby prevent the sample from becoming heated and the accuracy of measurement from becoming adversely affected. If, for example, a filter is inserted near the light source to cut off heat radiation outside the range of measurement such that there will be no significant rise in temperature to affect the result of measurement even if the sample is irradiated by a flux of light forming an image on the surface of the sample, it is permissible to cause an image of the optical stop 2 to be formed on the sample surface so as to clearly define the range of measurement. The integrating sphere 6 is a hollow spherical member having windows and a perfectly diffusing reflective inner surface made of a material with high reflectivity within the range of wavelengths used for the measurement and low dependence on wavelength such as barium sulfate coating, gold plating, fluorine resins and ceramics. Diffused and reflected light from the sample can be effectively captured by an integrating sphere thus structured.

On the side of the integrating sphere 6 from which light is made incident, there is disposed a dark vane 4 for intermittently shutting off the measuring light 18. The dark vane 4, for example, may be fan-shaped as shown in FIG. 3 and is controlled so as to be oscillated or rotated by a motor 5 as shown by an arrow, coupled with the analyzer's measuring operation. The measuring light 18 may be thereby screened, for example, such that the dark resistance or the dark current of the detector can be adjusted in the meantime. The optical system including the light source 1, the optical stop 2, the light-converging optical system 3, the dark vane 4 and the integrating sphere 6 is disposed on a base 11.

Samples in many different conditions may be placed at the integrating sphere, depending on the purpose of use of the analyzer. FIG. 1 shows a sample holder 7 in the form of a cup with a light-transmissive lid such that it may be filled with a powder sample such as wheat for measurement. The sample holder 7 is pressed against the sample window of the integrating sphere 6 to be affixed against it by a pressing means (not shown). Samples can be exchanged by opening and closing a lid 10 which forms a part of the housing 9 for the analyzer. If the sample is a vegetable or a fruit, and not in a powder form, the sample holder 7 need not be used and the sample itself may be directly attached to the sample window of the integrating sphere 6.

An entrance slit 15 for a spectrometer part 40 is positioned on the bottom surface of the integrating sphere 6. The spectrometer part 40 is attached to the bottom side of the base 11 near its edge. A diffraction grating 12 for diffracting and dispersing the incident light flux from the entrance slit 15 and a reflective mirror 13 for reflecting the dispersed light diffracted by the diffraction grating 12 to form dispersed images on a surface of an arrayed detector 14 are fixedly installed in the spectrometer part 40. The diffraction grating 12 is set so as to be able to look through the entrance slit 15 at a portion of the inner wall of the integrating sphere 6. In the illustrated example, the diffraction grating 12 is shown as a concave grating. Its aberration is adapted to be corrected by adjusting the separations and shape of its grooves. Such a diffraction grating can be manufactured mechanically by using a ruling engine or by a holographic method. The number of grooves and the blaze wavelength of the diffraction grating are determined by various factors required of the analyzer such as the range of wavelengths used for the measurement. The reflective mirror 13 is a planar mirror for changing the direction of diffracted light from the diffraction grating 12 once to direct it to the detector 14 and is not intended to directly contribute to the formation of images. It is a convenient instrument where it is difficult to direct the diffracted light from the diffraction grating 12 directly to the detector 14, depending, for example, on the size of the detector 14. It is convenient also for enabling the spectrometer part 40 to be made compact.

On the detector 14, the diffracted light is focused approximately on a plane. In the illustrated example, the magnification of the spectrometer is set approximately equal to 1:1 such that the size of the image formed on the detector surface is about the same as that of the entrance slit 15. The detector 14 comprises arrayed elements with sufficient sensitivity in the near infrared range of wavelengths used for the measurement. According to the illustrated example, it is formed with PbS elements arranged in an array on a single base board, but this is not intended to limit the scope of the invention. Use may equally well be made of semiconductor elements of InGaAs, InGaAsP or PtSi, for example. If the size of the image formed on the detector surface is about the same as that of the entrance slit 15, as in the illustrated example, the dimension of the entrance slit 15 in the direction of its height is determined by that of each element of the arrayed detector 14. Even if the slit 15 is made any larger in the direction of its height, the reflected light flux will spill over from the detector 14 and will not increase the total amount of received light. The dimension of the slit 15 in the direction of its width is determined by the design of the optical system based on the band width required by the analyzer.

FIG. 4 shows more in detail the arrayed detector 14 shown in FIG. 2 with PbS elements. This detector 14 is formed by attaching PbS elements 20 in an array on a base board 21 (for example, of quartz glass) through a pattern mask, pasting a cover glass piece 22 of quarts thereon and providing on its back surface a connector board for connection with wires from the individual PbS elements. Such arrayed PbS detectors are commercially available, for example, from Hamamatsu Photonics Company of Japan. Since PbS elements are not like an array of silicon photodiodes produced by the semiconductor integration technology, it is difficult to build within the element an electronic circuit such as a multiplexer. For this reason, it is common to take out wires from the individual elements forming an array. For this purpose, a base plate 23 is required for wiring and connectors 24 through which signals from the elements are taken outside. Thus, it is not always easy to reduce the total size of the arrayed detector and to direct the diffracted light from the grating 12 directly to the detector. As mentioned above, this problem can be solved by the use of the reflective mirror 13, and freedom of choice can be gained regarding the position for setting the arrayed detector.

The number of elements in the arrayed detector is selectively determined according to factors such as the band width, intervals between data and the range of wavelengths. For near infrared analyses, however, it is convenient to use about 256–512 elements. If 256 elements are used for the range of wavelengths 1100–2500 nm, the average range of wavelengths per element becomes about 5.5 nm/element, although the actual interval will depend on the wavelength. This pitch is much smaller than usually attainable by prior art devices requiring filters to be exchanged and is sufficient for near infrared analyses. The intervals between data can be easily made smaller by increasing the number of elements. Although the spectral band width per element of the diffracted light focused on the detector surface varies, depending on the characteristics of the diffraction grating itself and the design of the spectrometer, band widths which are sufficient for near infrared analyses at about 10nm can be obtained by proper designing.

With reference to FIG. 5, which shows approximately the structure of an example of signal processing system, signals from the individual PbS elements 20 of the arrayed detector are taken out through the base plate 23 and the connectors 24. A pre-amplifier 30 for amplifying a signal that has been taken out and an integrator 31 for integrating amplified signals for a specified length of time are provided to each of the elements. There is also provided a multiplexer 32 for sequentially retrieving integrated signals from the integrators 31 for the individual elements, and these sequentially retrieved signals are converted into digital signals and delivered to a CPU (central processing unit) 33 through an AD (analog-to-digital) converter 38. The CPU 33 serves to process received signals as measured data. Noise can be reduced to improve the accuracy of measurements by repeating several times the scanning process of amplifying and integrating signals from the elements and delivering them to the CPU 33 for digital integration of measured signals.

The CPU 33 is adapted not only to sequentially retrieve signals from the individual PbS elements 20 and to carry out data processing for re-structuring an absorption or reflection spectrum, but also to control circuits for controlling the dark vane 4 and the light source 1 (respectively referred to as the dark vane control circuit 34 and the light source control circuit 35), as well as to process the inputs from a keyboard 37 and to control the display of results of measurements on a CRT (cathode ray tube) screen 36. Measured data are seldom displayed in the form of a simple spectrum. It is more common to obtain quantitative or qualitative data as final results by applying a predictive formula on measured data. Such statistical processing may be carried out by the CPU 33 or, if the capability of the CPU is limited and not sufficient, use may be made of an independent personal computer.

Next, operations of the analyzer described above with reference to FIGS. 1–5 will be explained. Prior to the measurements of given samples, a standard diffusion-reflection plate, which has been separately prepared, is placed at the sample window of the integrating sphere 6. Measuring light is made incident on this standard plate and the data thus obtained are saved as standard values. Measurements can be made by comparing the transmission or reflection characteristics of each sample with the standard values obtained with the standard plate.

Each sample is carried on the sample holder 7 or directly placed at the position of the sample window of the integrating sphere 6. At the beginning, the motor 5 is activated such that the dark vane 4 screens the measuring light 18 from the source 1 and the surface of the sample 17 is dark. Each integrator 31, after being once reset, serves to integrate signals from the corresponding PbS element 20 for a predefined time interval. The integrated values, thus obtained and passed through the multiplexer 32, are sequentially converted into digital values by the AD converter 38 and received by the CPU 33. This series of data will be referred to as "the dark spectrum."

Next, the motor 5 is activated and the dark vane 4 is moved such that the measuring light 18 can pass through and the surface of the sample 17 is exposed to it. The measuring light 18 from the light source 1 is made convergent by means of the light-converging optical system 3 and irradiates the sample 17. Measuring light reflected by the sample 17 is trapped inside the integrating sphere 6 and undergoes multiple reflections on the inner wall surfaces of the integrating sphere 6. The reflected light from the sample, after such multiple reflections on the inner surfaces of the integrating sphere 6, is directed into the spectrometer part 40 through the entrance slit 15 on the bottom surface of the integrating sphere 6. It is diffracted by the diffraction grating 12 and received by the arrayed detector 14 by means of the reflective mirror 13. All light components with different wavelengths are received at the same time. The integrators 32 and the other components function as described above. This series of data may be referred to as "the apparent sample spectrum" because it contains signals totally unrelated to the measuring light 18 such as those due to the dark resistance of the PbS elements 20 in addition to the true sample spectrum.

Since the aforementioned dark spectrum is due entirely to the signals from the dark resistance, the true sample spectrum can be obtained by subtracting the dark spectrum from the apparent sample spectrum. A program for operating the components as described above and carrying out calculations is stored in the CPU 33.

Although the dark vane 4 and the motor 5 therefor are mechanically driven components, they do not have to be operated with the kind of accuracy required of prior art analyzers of the type described above with a mechanically driven diffracting grating. In other words, the dark vane 4 serves only to screen the measuring light 18 completely while a dark spectrum is being obtained and to allow it to pass through while an apparent sample spectrum is being obtained. As long as these two functions can be adequately carried out, no greater performance accuracy is required. For example, they are not even required to remain stationary while a measurement is being taken. Since no great accuracy is required, neither the dark vane 4 nor the motor 5 therefor has adverse effects on the reduction of time for measurement or on the reliability or dependability of the analyzer as a whole.

FIG. 6 shows another example of measuring section, characterized in that a sample 17a, which is positionally uniform (that is, the result of measurement does not depend on the position of irradiation), is exposed to a beam of white measuring light 18 to diffuse and reflect it. The diffusion-reflection characteristics of the sample can be measured as in the first example described above by making the incidence of light obliquely as above. In the example illustrated in FIG. 6, there is no need for an integrating sphere, which was necessary in the first example described above.

FIG. 7 shows still another example of measuring section, characterized in that the sample 17 is not placed opposite to the entrance window of an integrating sphere but is separated therefrom by 90° such that the measuring light 18 can irradiate a portion of the inner wall of the integrating sphere 6. According to the example illustrated in FIG. 7, the sample 17 is irradiated by light which has been diffused and reflected by the inner wall of the integrating sphere 6. A beam of reflected light in the direction of 0° from the sample thus irradiated by diffused light is directed through the entrance slit 15 into the spectroscope part by means of a converging lens 39. It is thereafter measured as in the first and second examples explained above. This example is advantageous in that errors in the measurement due to an increase in the temperature of the sample can be avoided because the sample is not directly irradiated by a strong beam of measuring light.

Although the invention has been described above with reference to examples wherein use was made of a detector with PbS elements aligned in an array, this is not intended to limit the scope of the invention. It is possible, for example, to simplify the structure of the signal processing system by using InGaAs elements produced by a semiconductor process to form the detector and forming the circuit of multiplexer, for example, on the same base plate as the detector.

In summary, the present invention makes it possible to electrically scan a wavelength band by sequentially retrieving signals from an arrayed detector placed on a plane on which diffused and reflected images are formed, while the diffraction grating in the spectrometer part is not mechanically scanned but remains fixed. Thus, high accuracy can be maintained for wavelength over a long period of time if initial adjustment is properly carried out. Moreover, the scanning of wavelengths can be carried out much more speedily than by mechanical methods. Thus, the present invention succeeds in providing near infrared analyzers capable of carrying out measurements quickly and improving accuracy of measurements by repeating measurements and integrating data thus obtained to thereby reduce noise.

What is claimed is:

1. A near infrared analyzer comprising:

a light source emitting a continuous spectrum of near infrared light;

an optical system for focusing the light emitted by said light source;

an integrating sphere for exposing a sample to the light emitted by said light source and focused by said optical system, said integrating sphere having an entrance window and a sample window, said optical system focusing said emitted light at one of said windows;

a spectrometer means having a diffraction grating and serving to disperse the light which has been passed through said integrating sphere and to focus the dispersed light on a detection plane;

an arrayed detector with sensitivity in a near infrared region, said arrayed detector being disposed at said detection plane; and a signal processing circuit for processing signals outputted from said arrayed detector.

2. The near infrared analyzer of claim 1 wherein said entrance and sample windows of said integrating sphere are formed diametrically opposite each other.

3. The near infrared analyzer of claim 2 wherein said entrance window is so positioned as to pass the light from said optical system therethrough, and wherein a sample holder supporting a sample is placed directly at said sample window.

4. The near infrared analyzer of claim 1 wherein said entrance and sample windows are separated from each other approximately by 90° with respect to said integrating sphere.

5. The near infrared analyzer of claim 1 wherein said light source emits a continuous spectrum of near infrared light approximately in the range of 1000–2600 nm in wavelength.

6. The near infrared analyzer of claim 1 wherein said diffraction grating is affixed to said spectrometer means so as to remain stationary during an operation of said analyzer.

7. The near infrared analyzer of claim 1 wherein said spectrometer means further includes a reflective mirror for reflecting the diffracted light from said diffraction grating and directing the reflected light to said arrayed detector.

8. The near infrared analyzer of claim 1 wherein said arrayed detector includes a single base plate and a plurality of arrayed PbS elements disposed on said base plate.

9. The near infrared analyzer of claim 8 wherein said arrayed detector further includes connectors for retrieving signals from said elements.

10. The near infrared analyzer of claim 1 wherein said signal processing circuit includes preamplifiers for amplifying signals received from said arrayed detector, integrating means for integrating the amplified signals for a specified length of time, a multiplexer for sequentially retrieving signals from said integrating means, and an analog-to-digital converter for converting analog signals retrieved by said multiplexer to digital signals.

11. The near infrared analyzer of claim 1 wherein said optical system directs said emitted light directly through said entrance window and focuses said emitted light at said sample window.

12. A near infrared analyzer comprising:

a light source emitting a continuous spectrum of near infrared light;

an integrating sphere having a single entrance window and a sample window;

an optical system for focusing said emitted light and directing said emitted light into said integrating sphere exclusively through said single entrance window and thereby exposing a sample to said directed light;

a spectrometer means having a diffraction grating and serving to disperse the light which has been passed through said integrating sphere and to focus the dispersed light on a detection plane;

an arrayed detector with sensitivity in a near infrared region, said arrayed detector being disposed at said detection plane; and a signal processing circuit for processing signals outputted from said arrayed detector.

13. The near infrared analyzer of claim 12 wherein said optical system focusses said emitted light at said single entrance window of said integrating sphere.

14. The near infrared analyzer of claim 12 wherein said light source emits a continuous spectrum of near infrared light approximately in the range of 1000–2600 nm in wavelength.

15. The near infrared analyzer of claim 12 wherein said diffraction grating is affixed to said spectrometer means so as to remain stationary during an operation of said analyzer.

16. The near infrared analyzer of claim 12 wherein said spectrometer means further includes a reflective mirror for reflecting the diffracted light from said diffraction grating and directing the reflected light to said arrayed detector.

17. The near infrared analyzer of claim 12 wherein said arrayed detector includes a single base plate and a plurality of arrayed PbS elements disposed on said base plate.

18. The near infrared analyzer of claim 17 wherein said arrayed detector further includes connectors for retrieving signals from said elements.

19. The near infrared analyzer of claim 12 wherein said signal processing circuit includes preamplifiers for amplifying signals received from said arrayed detector, integrating means for integrating the amplified signals for a specified length of time, a multiplexer for sequentially retrieving signals from said integrating means, and an analog-to-digital converter for converting analog signals retrieved by said multiplexer to digital signals.

20. The near infrared analyzer of claim 17 wherein said signal processing circuit includes preamplifiers for amplifying signals received individually from said arrayed elements, integrating means for integrating the amplified signals for a specified length of time, a multiplexer for sequentially retrieving signals from said integrating means, and an analog-to-digital converter for converting analog signals retrieved by said multiplexer to digital signals.

* * * * *